United States Patent
Ihara et al.

(10) Patent No.: US 7,361,675 B2
(45) Date of Patent: Apr. 22, 2008

(54) 1,2,4-THIADIAZOLE COMPOUNDS AND USE THEREOF

(75) Inventors: Hideki Ihara, Osaka (JP); Noriyasu Sakamoto, Osaka (JP)

(73) Assignee: Sumitomo Chemical Company Limited, Tokyo (JP)

( * ) Notice: Subject to any disclaimer, the term of this patent is extended or adjusted under 35 U.S.C. 154(b) by 558 days.

(21) Appl. No.: 10/530,136

(22) PCT Filed: Nov. 8, 2002

(86) PCT No.: PCT/JP02/11644

§ 371 (c)(1),
(2), (4) Date: Apr. 4, 2005

(87) PCT Pub. No.: WO2004/041798

PCT Pub. Date: May 21, 2004

(65) Prior Publication Data

US 2006/0167266 A1 Jul. 27, 2006

(51) Int. Cl.
*A01N 43/82* (2006.01)
*C07D 285/08* (2006.01)

(52) U.S. Cl. .................. 514/361; 548/125; 548/128; 548/129; 548/130

(58) Field of Classification Search ........... 548/125, 548/128, 129, 130; 514/361
See application file for complete search history.

(56) References Cited

U.S. PATENT DOCUMENTS 5,438,066 A    8/1995  Matthews
5,827,800 A *  10/1998 Forster et al. ............. 504/262
6,893,650 B1 * 5/2005  Charles et al. ............. 424/405

FOREIGN PATENT DOCUMENTS

| DE | 30 30 661 A1 | 4/1982 |
| EP | 0 534 219 A1 | 3/1993 |
| EP | 1 475 374 A1 | 11/2004 |
| JP | 06-100550 A | 4/1994 |
| JP | 2001-39954 A | 2/2001 |
| JP | 2002-338557 A | 11/2002 |

* cited by examiner

*Primary Examiner*—Golam M. M. Shameem
(74) *Attorney, Agent, or Firm*—Panitch Schwarze Belisario & Nadel LLP

(57) ABSTRACT

1,2,4-Thiadiazole compounds represented by the formula (1) have excellent control activities against harmful arthropods:

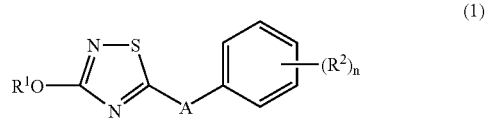

(1)

wherein $R^1$ represents C3-C7 alkynyl group optionally substituted one or more halogen atom(s); $R^2$ a represents a halogen atom, a C1-C4 alkyl group, a C1-C4 haloalkyl group, a C1-C4 alkoxy group, a C1-C4 haloalkoxy group, a C1-C4 alkylthio group, a cyano group, or a nitro group, and n is an integer of 0 to 5, provided that, when n is an integer of 2 or more, respective $R^2$s may be the same or different; A represents an oxygen atom, a sulfur atom, a single bond, a $CR^3R^4$ group, or $NR^5$; $R^3$ and $R^4$ represent each independently a hydrogen atom or a C1-4 alkyl group; and $R^5$ represent a hydrogen and the like.

10 Claims, No Drawings

1,2,4-THIADIAZOLE COMPOUNDS AND USE THEREOF

CROSS-REFERENCE TO RELATED APPLICATION

This application is a section 371 of International Application No. PCT/JP2002/011644, filed Nov. 8, 2002, which was published in the Japanese language on May 21, 2004, under International Publication No. WO 2004/041798 A1 and the disclosure of which is incorporated herein by reference.

TECHNICAL FIELD

The present invention relates to a 1,2,4-thiadiazole compound and use thereof.

BACKGROUND ART

It is known that a certain 1,3,4-thiadiazole compound can be used as an active ingredient of an agent for controlling harmful arthropods (DE3030661, etc.).

However, harmful arthropod controlling activity of this 1,3,4-thiadiazole compound is not sufficient, and a compound having more excellent harmful arthropod controlling activity is sought.

BRIEF SUMMARY OF THE INVENTION

The present inventor has studied intensively in order to find out a compound having excellent pesticidal activity, and have found excellent harmful arthropod controlling activity in a 1,2,4-thiadiazole compound. Thus, the present invention has been completed.

That is, the present invention provides a 1,2,4-thiadiazole compound represented by the formula (1):

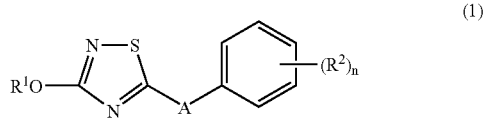

wherein $R^1$ represents a C3-C7 alkynyl group optionally substituted with one or more halogen atom(s), $R^2$ represents a halogen atom, a C1-C4 alkyl group, a C1-C4 haloalkyl group, a C1-C4 alkoxy group, a C1-C4 haloalkoxy group, a C1-C4 alkylthio group, a cyano group or a nitro group, n represents an integer of 0 to 5, provided that, when n represents an integer of 2 or more, respective $R^2$s may be the same or different, A represents an oxygen atom, a sulfur atom, a single bond, a $CR^3R^4$ group or a $NR^5$ group, $R^3$ and $R^4$ represent each independently a hydrogen atom or a C1-C4 alkyl group, and $R^5$ represents a hydrogen atom, a C1-C7 alkyl group, a haloalkyl group, a C2-C4(alkoxyalkyl) group, a C2-C4 (haloalkoxyalkyl) group, a C3-C6 alkenyl group, a C3-C6 haloalkenyl group, a C3-C7 alkynyl group, a C3-C7 haloalkynyl group or a cyanomethyl group (herein after referred to as the compound of the present invention); and an arthropod controlling composition containing the same as an active ingredient.

DETAILED DESCRIPTION OF THE INVENTION

In the compound of the present invention, examples of the C3-C7 alkynyl group optionally substituted with one or more halogen atom(s) represented by $R^1$ include a 2-propynyl group, a 2-butynyl group, a 4-fluoro-2-butynyl group, a 1-methyl-2-butynyl group, a 2-pentynyl group, a 4,4-dimethyl-2-pentynyl group, a 3-chloro-2-propynyl group, a 3-bromo-2-propynyl group, a 3-iodo-2-propynyl group, a 1-methyl-2-propynyl group, a 3-butynyl group, and a 3-pentynyl group.

Examples of the halogen atom represented by $R^2$ include a fluorine atom, a chlorine atom, and a bromine atom, examples of the C1-C4 alkyl group represented by $R^2$ include a methyl group, an ethyl group, and a 1,1-dimethylethyl group, examples of the C1-C4 haloalkyl group represented by $R^2$ include a trifluoromethyl group, a difluoromethyl group, and a pentafluoroethyl group, examples of the C1-C4 alkoxy group represented by $R^2$ include a methoxy group and an ethoxy group, examples of the C1-C4 haloalkoxy group represented by $R^2$ include a trifluoromethoxy group and a pentafluoroethoxy group, examples of the C1-C4 alkylthio group represented by $R^2$ include a methylthio group, and an ethylthio group.

Examples of the $CR^3R^4$ group represented by A include a $CH_2$ group, a $CH(CH_3)$ group, and examples of the $NR^5$ group represented by A include a NH group, a $NCH_3$ group, a $NC_2H_5$ group, a $NCH_2OCH_3$ group, a $NCH_2OC_2H_5$ group and a $NCH_2CN$ group.

Examples of the compound of the present invention include a 1,2,4-thiadiazole compound represented by the formula (1) wherein $R^1$ is a 2-propynyl group; a 1,2,4-thiadiazole compound represented by the formula (1) wherein $R^1$ is a 2-butynyl group; a 1,2,4-thiadiazole compound represented by the formula (1) wherein $R^1$ is a 2-pentynyl group; a 1,2,4-thiadiazole compound represented by the formula (1) wherein A is a single bond; a 1,2,4-thiadiazole compound represented by the formula (1) wherein $R^1$ is a 2-propynyl group, and A is a single bond; a 1,2,4-thiadiazole compound represented by the formula (1) wherein $R^1$ is a 2-butynyl group, and A is a single bond; a 1,2,4-thiadiazole compound represented by the formula (1) wherein $R^1$ is a 2-pentynyl group, and A is a single bond; a 1,2,4-thiadiazole compound represented by the formula (1) wherein n is 0; a 1,2,4-thiadiazole compound represented by the formula (1) wherein n is 1 or 2, and $R^2$ is a halogen atom.

Then, a process for preparing the compound of the present invention will be explained. The compound of the present invention can be prepared, for example, by reacting a compound represented by the formula (2) and $R^1OH$ in the presence of a base.

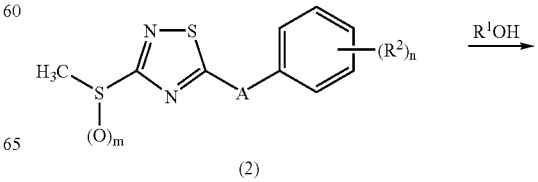

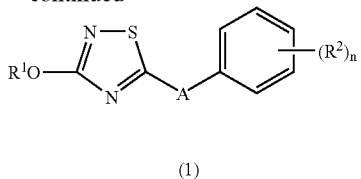

(1)

wherein A, $R^1$, $R^2$ and n are as defined above, and m represents 1 or 2.

The reaction is usually performed in a solvent. Examples of the solvent to be used include ethers such as tetrahydrofuran, acid amides such as N,N-dimethylformamide, dimethyl sulfoxide, and a mixture thereof. Examples of the base used in the reaction include inorganic bases such as sodium hydride, and the amount of the base is usually 1 to 2 mole relative to 1 mole of a compound represented by the formula (2). The amount of $R^1OH$ used in the reaction is usually 1 to 1.2 moles relative to 1 mole of a compound represented by the formula (2). The reaction temperature is usually in a range of 0 to 80° C., and the reaction time is usually in a range of 1 to 24 hours.

After completion of the reaction, the compound of the present invention can be obtained by subjecting the reaction mixture to post-treatment procedures such as organic solvent extraction, and concentration. If necessary, the compound of the present invention can be further purified by subjecting to procedures such as chromatography.

The compound represented by the formula (2) can be prepared by reacting a compound represented by the formula (3) with an oxidizing agent.

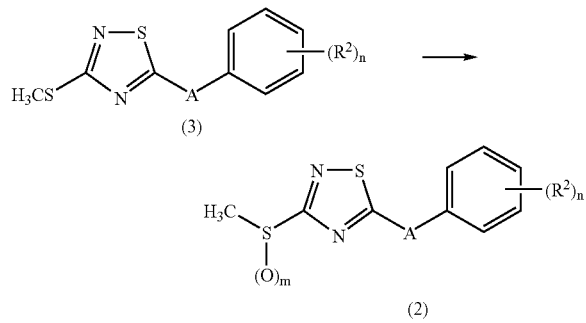

wherein A, $R^2$, n and m are as defined above.

The reaction is usually performed in a solvent. Examples of the solvent to be used include halogenated hydrocarbons such as chloroform and dichloromethane, and a mixture thereof. Examples of the oxidizing agent used in the reaction include peracids such as 3-chloroperoxybenzoic acid, and the amount of the oxidizing agent is usually 1 to 2.5 moles relative to 1 mole of the compound represented by the formula (3). The reaction temperature is usually in a range of −5° C. to room temperature, and the reaction time is usually in a range of 0.1 to 24 hours.

After completion of the reaction, the compound represented by the formula (2) can be obtained by subjecting the reaction mixture to post-treatment procedures such as organic solvent extraction, and concentration. If necessary, the compound can be further purified by subjecting to procedures such as chromatography.

The compound represented by the formula (3) can be prepared by any of the following methods of (I) to (IV) depending on a kind of A in the formula (3).

(I) A process for preparing a compound represented by the formula (3) in which A is a single bond, by reacting 5-chloro-3-methylthio-1,2,4-thiadiazole, and a phenylboronic acid compound represented by the formula (4) or a trialkylphenyltin compound represented by the formula (5) in the presence of a transition metal compound.

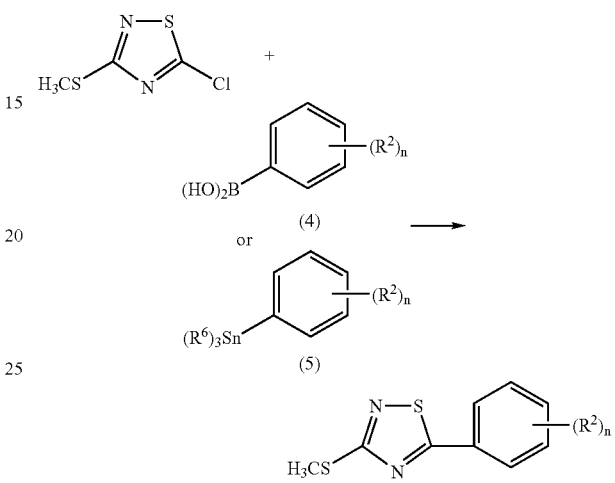

wherein $R^2$ and n are as defined above, and $R^6$ represents a C1-C4 alkyl group.

The reaction is usually performed in a solvent under an atmosphere of an inert gas (nitrogen, argon etc.). Examples of the solvent used in the reaction include alcohols such as methanol, ethanol and 2-propanol, ethers such as 1,2-dimethoxyethane, tetrahydrofuran, 1,4-dioxane, and methyl-t-butyl ether, aromatic hydrocarbons such as benzene and toluene, ketones such as acetone, acid amides such as N,N-dimethylformamide, water, and a mixture thereof. Examples of the transition metal compound used in the reaction include palladium (II) acetate, tetrakis(triphenylphosphine)palladium (0), {1,1'-bis(diphenylphosphino) ferrocene}dichloropalladium (II) and dichloro bis(triphenylphosphine)palladium(II), and the amount of the transition metal compound is usually 0.001 to 0.1 mole relative to 1 mole of 5-chloro-3-methylthio-1,2,4-thiadiazole. The amount of the phenylboronic acid compound represented by the formula (4) or the trialkylphenyltin compound represented by the formula (5) used in the reaction is usually 0.9 to 1.5 mole relative to 1 mole of 5-chloro-3-methylthio-1,2,4-thiadiazole. The reaction temperature of the reaction is usually in a range of room temperature to 150° C. The reaction time is usually in a range of 1 to 12 hours.

The reaction can be performed by adding a base, if necessary. Examples of the base which can be used include potassium phosphate, sodium carbonate, sodium bicarbonate, sodium acetate, potassium acetate and barium hydroxide. In addition, the reaction can be performed by adding a phase transfer catalyst, if necessary. Examples of the phase transfer catalyst which can be used include a quaternary ammonium salt such as tetrabutylammonium bromide, and benzyltrimethylammonium bromide.

After completion of the reaction, the objective product can be obtained by subjecting the reaction mixture to post-treatment procedures such as organic solvent extraction, and concentration. When the trialkylphenyltin compound represented by the formula (5) is used in the reaction, the objecte product can be obtained by adding an aqueous potassium fluoride solution to the reaction mixture, filtering the resulting precipitate, and concentrating the filtrate. The product can be further purified by subjecting to procedures such as chromatography, if necessary.

(II) A process for preparing a compound represented by the formula (3) in which A is an oxygen atom, a sulfur atom or a NH group, by reacting 5-chloro-3-methylthio-1,2,4-thiadiazole and a compound represented by the formula (6) in the presence of a base.

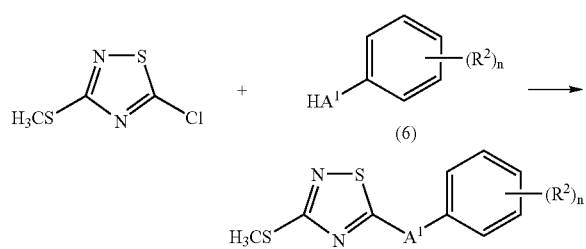

wherein $R^2$ and n are as defined above and $A^1$ represents an oxygen atom, a sulfur atom or a NH group.

The reaction is usually performed in a solvent, and examples of the solvent used in the reaction include ethers such as tetrahydrofuran, acid amides such as N,N-dimethylformamide, dimethyl sulfoxide, and a mixture thereof. Examples of the base used in the reaction include inorganic bases such as sodium hydride, and the amount of the base is usually 1 to 2 mole relative to 1 mole of 5-chloro-3-methylthio-1,2,4-thiadiazole. The amount of the compound represented by the formula (6) used in the reaction is usually 1 to 1.2 mole relative to 1 mole of 5-chloro-3-methylthio-1,2,4-thiadiazole. The reaction temperature is usually in a range of 0 to 80° C., and the reaction time is usually in a range of 1 to 24 hours.

After completion of the reaction, the objective product can be obtained by subjecting the reaction mixture to post-treatment procedures such as organic solvent extraction, and concentration. If necessary, the product can be further purified by subjecting to procedures such as chromatography.

(III) A process for preparing a compound represented by the formula (3) in which A is a $NR^5$ group, by reacting a compound represented by the formula (3) in which A is a NH group with $R^5X$ in the presence of a base.

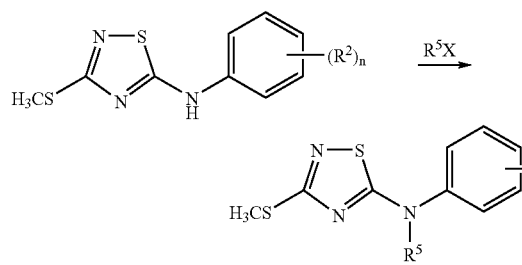

wherein $R^2$, $R^5$ and n are as defined above, and X represents a halogen atom.

The reaction is usually performed in a solvent. Examples of the solvent used in the reaction include ethers such as tetrahydrofuran, acid amides such as N,N-dimethylformamide, dimethyl sulfoxide, and a mixture thereof. Examples of the base used in the reaction include inorganic bases such as sodium hydride, and the amount of the base is usually 1 to 2 mole relative to 1 mole of a compound represented by the formula (3) in which A is a $NR^5$ group. The amount of $R^5X$ used in the reaction is usually 1 to 1.2 mole relative to 1 mole of a compound represented by the formula (3) in which A is a $NR^5$ group. The reaction temperature is usually in a range of 0 to 80° C., and the reaction time is usually in a range of 1 to 12 hours.

After completion of the reaction, the objective product can be obtained by subjecting the reaction mixture to post-treatment procedures such as organic solvent extraction, and concentration. If necessary, the product can be further purified by subjecting to procedures such as chromatography.

(IV) A process for preparing a compound represented by the formula (3), wherein A is a $CR^3R^4$ group, by reacting 5-chloro-3-methylthio-1,2,4-thiadiazole and a compound represented by the formula (7) in the presence of a transition metal compound.

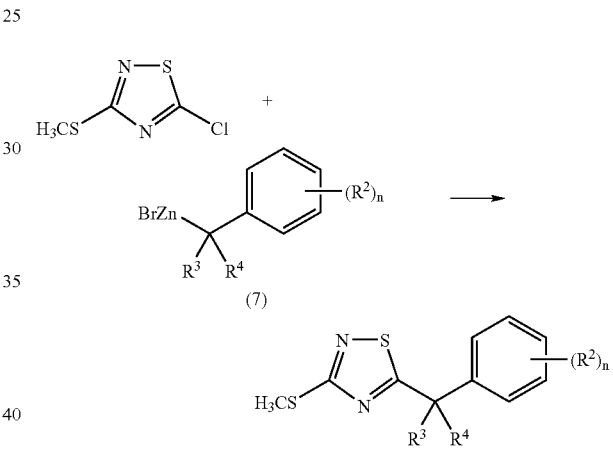

wherein $R^{2'}$ $R^3$, $R^4$ and n are as defined above.

The reaction is usually performed in a solvent, and examples of the solvent used in the reaction include ethers such as tetrahydrofuran, acid amides such as N,N-dimethylformamide, dimethyl sulfoxide, and a mixture thereof.

Examples of the transition metal compound used in the reaction include tetrakis(triphenylphosphine)palladium (0), {1,1'-bis(diphenylphosphino)ferrocene}dichloropalladium (II) and dichloro bis(triphenylphosphine)palladium (II), and the amount of the transition metal compound is usually 0.001 to 0.1 mole relative to 1 mole of 5-chloro-3-methylthio-1,2,4-thiadiazole.

The amount of a compound represented by the formula (7) used in the reaction is usually 1 to 1.2 mole relative to 1 mole of 5-chloro-3-methylthio-1,2,4-thiadiazole.

The reaction temperature is usually in a range of 0 to 80° C., and the reaction time is usually in a range of 1 to 24 hours.

After completion of the reaction, the objective product can be obtained by subjecting the reaction mixture to post-treatment procedures such as organic solvent extraction, and concentration. If necessary, the product can be further purified by subjecting to procedures such as chromatography.

Then, specific examples of the compound of the present invention are shown in Table 1.

TABLE 1

Compound represented by the formula (1):

$$R^1O-\underset{N}{\overset{N-S}{\diagdown}}-A-\underset{}{\overset{}{\bigcirc}}-(R^2)_n \quad (1)$$

| Compound No. | R¹ | (R²)ₙ | A |
|---|---|---|---|
| 1 | 2-propynyl | Unsubstituted | Single bond |
| 2 | 2-butynyl | Unsubstituted | Single bond |
| 3 | 2-pentynyl | Unsubstituted | Single bond |
| 4 | 4,4-dimethyl-2-pentynyl | Unsubstituted | Single bond |
| 5 | 2-butynyl | 2-fluoro | Single bond |
| 6 | 2-butynyl | 3-fluoro | Single bond |
| 7 | 2-butynyl | 4-fluoro | Single bond |
| 8 | 2-butynyl | 2-chloro | Single bond |
| 9 | 2-butynyl | 3-chloro | Single bond |
| 10 | 2-butynyl | 4-chloro | Single bond |
| 11 | 2-butynyl | 2,4-difluoro | Single bond |
| 12 | 2-butynyl | 2,5-difluoro | Single bond |
| 13 | 2-butynyl | 2,6-difluoro | Single bond |
| 14 | 2-butynyl | 3,4-difluoro | Single bond |
| 15 | 2-butynyl | 3,5-difluoro | Single bond |
| 16 | 2-butynyl | 2,3-difluoro | Single bond |
| 17 | 2-butynyl | 2-methyl | Single bond |
| 18 | 2-butynyl | 3-methyl | Single bond |
| 19 | 2-butynyl | 4-methyl | Single bond |
| 20 | 2-butynyl | 4-tert-butyl | Single bond |
| 21 | 2-butynyl | 3,5-bistrifluoromethyl | Single bond |
| 22 | 2-butynyl | Unsubstituted | Oxygen atom |
| 23 | 2-butynyl | 2-fluoro | Oxygen atom |
| 24 | 2-butynyl | 3-fluoro | Oxygen atom |
| 25 | 2-butynyl | 4-fluoro | Oxygen atom |
| 26 | 2-butynyl | 2-chloro | Oxygen atom |
| 27 | 2-butynyl | 3-chloro | Oxygen atom |
| 28 | 2-butynyl | 4-chloro | Oxygen atom |
| 29 | 2-butynyl | 2,4-difluoro | Oxygen atom |
| 30 | 2-butynyl | 2,5-difluoro | Oxygen atom |
| 31 | 2-butynyl | 2,6-difluoro | Oxygen atom |
| 32 | 2-butynyl | 3,4-difluoro | Oxygen atom |
| 33 | 2-butynyl | 3,5-difluoro | Oxygen atom |
| 34 | 2-butynyl | 2,3-difluoro | Oxygen atom |
| 35 | 2-butynyl | 2-methyl | Oxygen atom |
| 36 | 2-butynyl | 3-methyl | Oxygen atom |
| 37 | 2-butynyl | 4-methyl | Oxygen atom |
| 38 | 2-butynyl | 4-tert-butyl | Oxygen atom |
| 39 | 2-butynyl | 3,5-bistrifluoromethyl | Oxygen atom |
| 40 | 2-butynyl | Unsubstituted | CH₂ |
| 41 | 2-butynyl | 2-fluoro | CH₂ |
| 42 | 2-butynyl | 3-fluoro | CH₂ |
| 43 | 2-butynyl | 4-fluoro | CH₂ |
| 44 | 2-butynyl | 2-chloro | CH₂ |
| 45 | 2-butynyl | 3-chloro | CH₂ |
| 46 | 2-butynyl | 4-chloro | CH₂ |
| 47 | 2-butynyl | 2,4-difluoro | CH₂ |
| 48 | 2-butynyl | 2,5-difluoro | CH₂ |
| 49 | 2-butynyl | 2,6-difluoro | CH₂ |
| 50 | 2-butynyl | 3,4-difluoro | CH₂ |
| 51 | 2-butynyl | 2-chloro | CH₂ |
| 52 | 2-butynyl | 3-chloro | CH₂ |
| 53 | 2-butynyl | 4-chloro | CH₂ |
| 54 | 2-butynyl | 2,4-difluoro | CH₂ |
| 55 | 2-butynyl | 2,5-difluoro | CH₂ |
| 56 | 2-butynyl | 2,6-difluoro | CH₂ |
| 57 | 2-butynyl | 3,4-difluoro | CH₂ |
| 58 | 2-butynyl | 3,5-difluoro | CH₂ |
| 59 | 2-butynyl | 2,3-difluoro | CH₂ |
| 60 | 2-butynyl | 2-methyl | CH₂ |
| 61 | 2-butynyl | 3-methyl | CH₂ |

TABLE 1-continued

Compound represented by the formula (1):

$$R^1O-\underset{N}{\overset{N-S}{\diagdown}}-A-\underset{}{\overset{}{\bigcirc}}-(R^2)_n \quad (1)$$

| Compound No. | R¹ | (R²)ₙ | A |
|---|---|---|---|
| 62 | 2-butynyl | 4-methyl | CH₂ |
| 63 | 2-butynyl | 4-tert-butyl | CH₂ |
| 64 | 2-butynyl | 3,5-bistrifluoromethyl | CH₂ |
| 65 | 2-butynyl | Unsubstituted | NH |
| 66 | 2-butynyl | Unsubstituted | NCH₃ |
| 67 | 2-butynyl | Unsubstituted | NCH₂CH₃ |
| 68 | 2-butynyl | Unsubstituted | NCH₂OCH₃ |
| 69 | 2-butynyl | Unsubstituted | NCH₂OC₂H₅ |
| 70 | 1-methyl-2-butynyl | Unsubstituted | Single bond |
| 71 | 1-methyl-2-butynyl | Unsubstituted | Oxygen atom |
| 72 | 1-methyl-2-butynyl | 2-fluoro | Single bond |
| 73 | 4-fluoro-2-butynyl | Unsubstituted | Single bond |
| 74 | 2-pentynyl | 2-fluoro | Single bond |
| 75 | 2-pentynyl | 3-fluoro | Single bond |
| 76 | 2-pentynyl | 4-fluoro | Single bond |
| 77 | 2-pentynyl | 2-chloro | Single bond |
| 78 | 2-pentynyl | 3-chloro | Single bond |
| 79 | 2-pentynyl | 4-chloro | Single bond |
| 80 | 2-pentynyl | 2,4-difluoro | Single bond |
| 81 | 2-pentynyl | 2,5-difluoro | Single bond |
| 82 | 2-pentynyl | 2,6-difluoro | Single bond |
| 83 | 2-pentynyl | 3,4-difluoro | Single bond |
| 84 | 2-pentynyl | 3,5-difluoro | Single bond |
| 85 | 2-pentynyl | 2,3-difluoro | Single bond |
| 86 | 2-pentynyl | 2-methyl | Single bond |
| 87 | 2-pentynyl | 3-methyl | Single bond |
| 88 | 2-pentynyl | 4-methyl | Single bond |
| 89 | 2-pentynyl | 4-tert-butyl | Single bond |
| 90 | 2-pentynyl | 3,5-bistrifluoromethyl | Single bond |
| 91 | 2-butynyl | 4-fluoro-3-methyl | Single bond |
| 92 | 2-butynyl | 4-methyl-3-nitro | Single bond |
| 93 | 2-butynyl | 4-methylthio | Single bond |
| 94 | 2-butynyl | 2-methoxy | Single bond |
| 95 | 2-butynyl | 3-methoxy | Single bond |
| 96 | 2-butynyl | 4-methoxy | Single bond |
| 97 | 2-butynyl | 2,3-dimethyl | Single bond |
| 98 | 2-butynyl | 3,5-dimethyl | Single bond |
| 99 | 2-butynyl | 2,5-dimethyl | Single bond |
| 100 | 2-butynyl | 3,5-dibromo | Single bond |
| 101 | 2-butynyl | 3-chloro-4-fluoro | Single bond |
| 102 | 2-butynyl | 2,4-dichloro | Single bond |
| 103 | 2-butynyl | 2,3-dichloro | Single bond |
| 104 | 2-butynyl | 2,5-dichloro | Single bond |
| 105 | 2-butynyl | 3,4-dichloro | Single bond |
| 106 | 2-butynyl | 3,5-dichloro | Single bond |
| 107 | 2-butynyl | 2-bromo | Single bond |
| 108 | 2-butynyl | 3-bromo | Single bond |
| 109 | 2-butynyl | 4-bromo | Single bond |
| 110 | 2-butynyl | 3-nitro | Single bond |
| 111 | 2-butynyl | 4-trifluoromethyl | Single bond |
| 112 | 2-butynyl | 3-trifluoromethoxy | Single bond |
| 113 | 2-butynyl | 4-trifluoromethoxy | Single bond |
| 114 | 2-butynyl | 3-cyano | Single bond |
| 115 | 2-butynyl | 4-cyano | Single bond |
| 116 | 2-pentynyl | 4-fluoro3-methyl | Single bond |
| 117 | 2-pentynyl | 4-methyl-3-nitro | Single bond |
| 118 | 2-pentynyl | 4-methylthio | Single bond |
| 119 | 2-pentynyl | 2-methoxy | Single bond |
| 120 | 2-pentynyl | 3-methoxy | Single bond |
| 121 | 2-pentynyl | 4-methoxy | Single bond |
| 122 | 2-pentynyl | 2,3-dimethyl | Single bond |

TABLE 1-continued

Compound represented by the formula (1):

$$R^1O-\underset{N}{\underset{\|}{C}}\overset{N-S}{\underset{A}{\diagdown/}}-\!\!\!\!\!\!\!\!\!\!\!\!\!\!\!\!\!\!\!\!\!\!\!\!\!-(R^2)_n \quad (1)$$

| Compound No. | R¹ | (R²)ₙ | A |
|---|---|---|---|
| 123 | 2-pentynyl | 3,5-dimethyl | Single bond |
| 124 | 2-pentynyl | 2,5-dimethyl | Single bond |
| 125 | 2-pentynyl | 3,5-dibromo | Single bond |
| 126 | 2-pentynyl | 3-chloro-4-fluoro | Single bond |
| 127 | 2-pentynyl | 2,4-dichloro | Single bond |
| 128 | 2-pentynyl | 2,3-dichloro | Single bond |
| 129 | 2-pentynyl | 2,5-dichloro | Single bond |
| 130 | 2-pentynyl | 3,4-dichloro | Single bond |
| 131 | 2-pentynyl | 3,5-dichloro | Single bond |
| 132 | 2-pentynyl | 2-bromo | Single bond |
| 133 | 2-pentynyl | 3-bromo | Single bond |
| 134 | 2-pentynyl | 4-bromo | Single bond |
| 135 | 2-pentynyl | 3-nitro | Single bond |
| 136 | 2-pentynyl | 4-trifluoromethyl | Single bond |
| 137 | 2-pentynyl | 3-trifluoromethoxy | Single bond |
| 138 | 2-pentynyl | 4-trifluoromethoxy | Single bond |
| 139 | 2-pentynyl | 3-cyano | Single bond |
| 140 | 2-pentynyl | 4-cyano | Single bond |

Examples of the harmful arthropod against which the compound of the present invention exhibits controlling effect are insects and mites, specifically, following ones.

Hemiptera insect pest: planthoppers such as small brown planthopper (*Laodelphax striatellus*), brown planthopper (*Nilaparvata lugens*) and white-backed rice planthopper (*Sogatella furcifera*), leafhoppers such as green rice leafhopper (*Nephotettix cincticeps*) and tea green leafhopper (*Empoasca onukii*), aphids such as cotton aphid (*Aphis gossypii*) and green peach aphid (*Myzus persicae*), stink bugs, whiteflies such as greenhouse whitefly (*Trialeurodes vaporariorum*), sweet-potato whitefy (*Bemisia tabaci*) and silverleaf whitefly (*Bemisia* argentifolii), scales, lace bugs, jumping plantlice, etc.

Lepidoptera insect pest: pyralid moths such as rice stem borer (*Chilo suppressalis*), rice leafroller (*Cnaphalocrocis medinalis*), European corn borer (*Ostrinia nubilalis*) and bluegrass webworm (Parapediasia teterrella), owlet moths such as tabaco cutworm (*Spodoptera litura*), *Spodoptera exigua*, rice armyworm (*Pseudaletia separata*), cabbage armyworm (*Mamestra brassicae*), black cutworm (*Agrotis ipsilon*), *Trichoplusia* spp., *Heliothis* spp., *Helicoverpa* spp. and *Earias* spp., whites and sulfer butterflies such as common cabbage worm (*Pieris rapae* crucivora), tortricid moths such as *Adoxophyes orana* fasciata, *Grapholita molesta* and codling moth (*Cydia pomonella*), Carposimidae such as peach fruit moth (*Carposina niponensis*), Bucculatricidae such as Lyonetia clerkella, leaf-blotch miners such as *Phyllonorycter* ringoniella, Phyllochistinae such as Phyllocnistis citrella, Yponomeutidae such as diamondback moth (Plutela xylostella), gelechid moths such as pink ball worm (*Pectinophora gossypiella*), Arctiidae, clothes moths, etc.

Diptera insect pest: mosquitos such as common mosquito (*Culex pipiens* pallens), oriental latrine fly (*Culex tritaeniorhynchus*) and southern house mosquito (*Culex quinquefasciatus*), *Aedes* spp. such as *Aedes aegypti* and *Aedes albopictus*, *Anophles* spp. such as *Anopheles sinensis*, midges, house flies such as housefly (*Musca domestica*) and false stablefly (Muscina stabulans), Calliphoridae, Sarcophagidae, little housefly, Anthomyiidae such as seedcrn maggot (*Delia platura*) and onion maggot (*Delia antiqua*), fruit flies, small fruit flies, moth flies, black flies, Tabanidae, stable flies, leafminer flies, etc.

Coleoptera insect pest: corn rootworm such as western corn rootworm (*Diabrotica virgifera virgifera*) and southern corn rootworm (*Diabrotica undecimpunctata howardi*), scarabs such as cupreous chafer (*Anomala cuprea*) and soybean beetle (*Anomala* rufocuprea), weevils such as maize weevil (*Sitophilus zeamais*), ricewater weevil (*Lissorhoptrus oryzophilus*) and adzuki bean weevil (Callosobruchuys chienensis), darkling beetles such as yellow mealworm (*Tenebrio molitor*) and red flour beetles (*Tribolium castaneum*), leaf beetles such as *Oulema oryzae*, cucurbit leaf beetle (*Aulacophora femoralis*), striped flea beetle (*Phyllotreta striolata*) and Colorado beetle (*Leptinotarsa decemlineata*), Anbiidae, *Epilachna* spp. such as twenty-eight-spotted ladbirds (*Epilachna* vigintioctopunctata), powderpost beetles, false powderpost beetles, long-horned beetles, Paederus fuscipes, etc.

Thysanoptera insect pest: thrips such as *Thrips* spp. such as *Thrips palmi*, *Frankliniella* spp. such as western flower thrips (*Frankliniella occidentalis*), *Sciltothrips* ssp. such as yellow tea thrips (*Sciltothrips dorsalis*), Plaeothripidae, etc.

Hymenoptera insect pest: saufliws, ants, hornets, etc.

Dictyoptera insect pest: cockroachs, German cockroachs, etc.

Orthoptera insect pest: glasshoppers, mole crickets, etc.

Siphonaptera insect pest: feas, etc.

Anoplura insect pest: human body louse, etc.

Isoptera insect pest: termites, etc.

Acarina insect pest: spider mites etc.

The compound of the present invention has characteristic in controlling effect against Hemiptera insect pests, Lepidopterta insect pests, Coleoptera insect pests and Thysanoptera insect pest.

The harmful arthropod controlling composition of the present invention may be the compound of the present invention itself. Usually, the compound of the present invention and, for example, a solid carrier, a liquid carrier, a gaseous carrier and/or a bait (base material for poison bait) are mixed, a surfactant and other adjuvants for formulation are added if necessary, and they are formulated into, for example, oils, emulsions, flowables, granules, powders, poison baits or microcapsules to obtain the harmful arthropod controlling composition of the present invention. The formulation usually contains 0.01 to 95% by weight of the compound of the present invention.

Examples of the solid carrier used for formulation into the composition include fine powders or particles such as clays (kaolin clay, diatomaceous earth, synthetic hydrated silicon oxide, bentonite, fubasami clay, acid clay etc.), talc, ceramics, other inorganic minerals (sericite, quarts, sulfur, active carbon, calcium carbonate, hydrated silica etc.), and chemical fertilizers (ammonium sulfate, ammonium phosphate, ammonium nitrate, urea, ammonium chloride, etc.). Examples of the liquid carrier include water, alcohols (methanol, ethanol, etc.), ketones (acetone, methyl ethyl ketone, etc.), aromatic hydrocarbons (benzene, toluene, xylene, ethylbenzene, methylnaphthalene, etc.), aliphatic hydrocarbons (hexane, cyclohexane, kerosene, light oil, etc.), esters (ethyl acetate, butyl acetate, etc.), nitrites (acetonitrile, isobutyronitrile, etc.), ethers (diisopropyl ether, dioxane, etc.), acid amides (N,N-dimethylformamide, N,N-dimethylacetamide, etc.), halogenated hydrocarbons (dichloromethane, trichloroethane carbon tetrachloride, etc.), dimethyl sulfoxide, and vegetable oils (soybean oil, cottonseed oil, etc.), and examples of the gaseous carrier include fluorocarbon, butane gas, LPG (liquefied petroleum gas), dimethyl ether and carbon dioxide gas. Examples of a surfactant include alkyl sulfate salts, alkyl sulfonic acid salts, alkylaryl sulfonic acid salts, alkylaryl ethers and their polyoxyethylene derivatives, polyethylene glycols ethers, polyhydric alcohol esters and sugar alcohol derivatives. Examples of adjuvants for formulation include sticker, dispersants and stabilizers, specifically, casein, gelatin, polysaccharides (starch powder, gum arabic, cellulose derivative, alginic acid etc.), lignin derivative, bentonite, sugars, synthetic water-soluble polymers (polyvinyl alcohol, polyvinylpyrrolidone, polyacrylic acid, etc.), PAP (acidic isopropyl phosphate), BHT (2,6-di-tert-butyl-4-methylphenol), BHA (mixture of 2-tert-butyl-4-methoxyphenol and 3-tert-butyl-4-methoxyphenol), vegetable oil, mineral oil, fatty acid and fatty acid ester. Examples of the base of a poison bait include a bait ingredient such as cereal powder, vegetable oil, sugar and crystalline cellulose, and antioxidant such as dibutylhydroxytoluene and nordihydroguaialetic acid, preservative such as dehydroacetic acid, agent for preventing erroneous eating by children or pets such as red pepper powder, and insect pest attracting perfume such as cheese perfume, onion perfume, and peanuts oil.

The harmful arthropod controlling composition of the present invention is used by applying to harmful arthropods or a place where harmful arthropods inhibit. For example, when a harmful arthropod parasitizing a cultivating plant is controlled, the arthropod can be controlled by scattering the harmful arthropod controlling composition of the present invention on a ground part of the cultivating plant, or by pouring the harmful arthropod controlling composition of the present invention over a root part of the cultivating plant.

When the harmful arthropod controlling composition of the present invention is used, the application amount is usually 0.1 to 1,000 g per 1,000 m$^2$ in terms of the compound of the present invention. Emulsions, wettable powders, flowables and microcapsules are usually applied by diluting with water so that the active ingredient concentration becomes 10 to 10,000 ppm, and granules and powders are usually applied as they are.

Alternatively, the harmful arthropod controlling composition of the present invention can be used together with other insecticide, nematicide, acaricide, fungicide, herbicide, plant growth regulating agent, synergist, fertilizer, soil conditioner, animal feed, etc.

Examples of such insecticide, acaricide and nematicide include organophosphorous compounds such as fenitrothion, fenthion, pyridafenthion, diazinon, chlorpyrifos, chlorpyrifos-methyl, acephate, methidathion, disulfoton, DDVP, sulprofos, profenofos, cyanophos, dioxabenzofos, dimethoate, phenthoate, malathion, trichlorfon, azin phosmethyl, monocrotophos, dicrotophos, ethion, fosthiazate; carbamate compounds such as BPMC, benfuracarb, propoxur, carbo sulfan, carbaryl, methomyl, ethiofencarb, aldicarb, oxamyl, fenothiocarb, and thiodicarb; pyrethroid compounds such as etofenprox, fenvalerate, esfenvalerate, fenpropathrin, cypermethrin, α-cypermethrin, Z-cypermethrin, permethrin, cyhalothrin, λ-cyhalothrin, cyfluthrin, β-cyfluthrin, deltamethrin, cycloprothrin, τ-fluvalinate, flucythrinate, bifenthrin, acrinathrin, tralomethrin, silafluofen and halfenprox; neonicotinoid compound such acetamiprid, thiamethoxam and thiacloprid; benzoylphenylurea compounds such as chlorfluazuron, teflubenzuron, fulfenoxuron and lufenuron; benzoylhydrazide compounds such as tebufenozide, holofenozide, methoxyfenozide and chromafenozide; thiadiazine compounds such as buprofezin; nereistoxin compounds such as cartap, thiocyclam, bensultap; chlorinated hydrocarbon compounds such as endosulfan, γ-BHC, and 1,1-bis(chlorophenyl)-2,2,2-trichloroethanol; formamidine compounds such as amitraz, and chlordimeform; thiourea compounds such as diafenthiuron; phenylpyrazole compounds; chlorfenapyr, pymetrozine, spinosad, indoxacarb, bromopropylate, tetradifon, chinomethionat, propargite, fenbutatin oxide, hexythiazox, etoxazole, clofentezine, pyridaben, fenpyroximate, tebufenpyrad, pyrimidifen, fenazaquin, acequinocyl, bifenazate, fluacrypyrim, spirodichlofen, milbemectin, avermectin, emamectin benzoate, azadirachtin[AZAD], polynactine complex [tetranactin, dinactin, trinactin].

The present invention will be explained more detail below by way of Preparation Examples, Formulation Examples and Test Examples, but the present invention is not limited to these examples. In addition, $^1$H-NMR data in Preparation Examples, and Reference Preparation Examples were measured in deuteride chloroform solvent using tetramethylsilane as an internal standard. In Preparation Examples, No. of the compound of the present invention indicates that shown in aforementioned Table 1.

PREPARATION EXAMPLE 1

To 3 ml of N,N-dimethylformamide were added 160 mg of a mixture of 3-methylsulfinyl-5-phenyl-1,2,4-thiadiazole and 3-methylsulfonyl-5-phenyl-1,2,4-thiadiazole (integration ratio of $^1$H-NMR sulfonyl form:sulfinyl form=4:1) and 60 mg of propargyl alcohol, and to the resulting mixture was added 43 mg of sodium hydride (60% oily) with ice-cooling. The mixture was stirred for 20 minutes with ice-cooling, and allowed to stand at room temperature for 18 hours. Then, the reaction mixture was poured into an aqueous saturated sodium chloride solution, and the mixture was extracted with t-butyl methyl ether. The organic layer was concentrated, and the resulting residue was subjected to silica gel column chromatography to obtain 100 mg of 5-phenyl-3-propargyloxy-1,2,4-thiadiazole (the compound (1) of the present invention).

mp: 66.9° C.

$^1$H-NMR: 2.55 (t, 1H), 5.10 (d, 2H), 7.48-7.54 (m, 3H), 7.91-7.94 (m, 2H)

PREPARATION EXAMPLE 2

To 3 ml of N,N-dimethylformamide were added 300 mg of a mixture of 3-methylsulfinyl-5-phenyl-1,2,4-thiadiazole and 3-methylsulfonyl-5-phenyl-1,2,4-thiadiazole (integration ratio of $^1$H-NMR sulfonyl form:sulfinyl form=4:1) and 141 mg of 2-butyne-1-ol, and to the resulting mixture was added 80 mg of sodium hydride (60% oily) with ice-cooling. The mixture was stirred for 10 minutes with ice-cooling, and allowed to stand at room temperature for 18 hours. Then, the reaction mixture was poured into an aqueous saturated sodium chloride solution, and the mixture was extracted with t-butyl methyl ether. The organic layer was concentrated, and the resulting residue was subjected to silica gel column chromatography to obtain 200 mg of 5-phenyl-3-(2-butynyloxy)-1,2,4-thiadiazole (the compound (2) of the present invention).

mp: 70.3° C.

$^1$H-NMR: 1.88 (t, 3H), 5.05 (q, 2H), 7.45-7.53 (m, 3H), 7.91-7.93 (m, 2H)

PREPARATION EXAMPLE 3

3-Methylthio-5-(2,3-difluorophenyl)-1,2,4-thiadiazole was dissolved in 14 ml of chloroform, and 279 mg of m-chloroperoxybenzoic acid (65%<) was added thereto. The mixture was stirred for 7 hours with ice-cooling, and allowed to stand at room temperature overnight. Then, the reaction mixture was added to an aqueous sodium bicarbonate solution, and layers were separated. The organic layer was concentrated. Further, toluene was added to the residue, and the mixture was concentrated. To the resulting residue were added 2 ml of N,N-dimethylformamide and 59 mg of 2-butyne-1-ol, and 59 mg of sodium hydride (60% oily) was added thereto with ice-cooling. The mixture was stirred at the same temperature for 30 minutes, and further stirred at room temperature for 3 hours. Then, the reaction mixture was poured into an aqueous saturated sodium chloride solution, and the mixture was extracted with t-butyl methyl ether. The residue obtained by concentration of the organic layer was purified by silica gel column chromatography to obtain 95 mg of 5-(2,3-difluorophenyl)-3-(2-butynyloxy)-1,2,4-thiadiazole (the compound (16) of the present invention).

$^1$H-NMR: 1.88 (t, 3H), 5.07 (q, 2H), 7.24-7.36 (m, 2H), 8.04-8.09 (m, 1H)

PREPARATION EXAMPLE 4

To 2 ml of N,N-dimethylformamide were added 295 mg of a mixture of 3-methylsulfinyl-5-(2-fluorophenyl)-1,2,4-thiadiazole and 3-methylsulfonyl-5-(2-fluorophenyl)-1,2,4-thiadiazole (integration ratio of $^1$H-NMR sulfonyl form: sulfinyl form=4:1) and 85 mg of 2-butyne-1-ol, to the resulting mixture was added 55 mg of sodium hydride (60% oily) with ice-cooling, and the mixture was stirred for 10 minutes, and further stirred at room temperature for 3 hours. The reaction mixture was poured into an aqueous saturated sodium chloride solution, and the mixture was extracted with t-butyl methyl ether. The organic layer was concentrated, and the residue was subjected to silica gel column chromatography to obtain 227 mg of 5-(2-fluorophenyl)-3-(2-butynyloxy)-1,2,4-thiadiazole (the compound (5) of the present invention).

$^1$H-NMR: 1.88 (t, 3H), 5.07 (q, 2H), 7.20-7.33 (m, 2H), 7.48-7.56 (m, 1H), 8.29-8.35 (m, 1H)

PREPARATION EXAMPLE 5

In 3 ml of N,N-dimethylformamide, 350 mg of 3-methylsulfonyl-5-(3-fluorophenyl)-1,2,4-thiadiazole and 105 mg of 2-butyne-1-ol were dissolved, to the resulting solution was added 65 mg of sodium hydride (60% oily) with ice-cooling, and the mixture was stirred for 10 minutes, and further stirred at room temperature for 4 hours. Then, the reaction mixture was poured into an aqueous saturated sodium chloride solution, and the mixture was extracted with t-butyl methyl ether. The residue obtained by concentration of the organic layer was subjected to silica gel column chromatography to obtain 289 mg of 5-(3-fluorophenyl)-3-(2-butynyloxy)-1,2,4-thiadiazole (the compound (6) of the present invention).

mp: 68.7° C.

$^1$H-NMR: 1.88 (t, 3H), 5.06 (q, 2H), 7.12-7.25 (m, 1H), 7.42-7.50 (m, 1H), 7.64-7.70 (m, 1H)

PREPARATION EXAMPLE 6

In 2.5 ml of N,N-dimethylformamide, 350 mg of 3-methylsulfonyl-5-(3-chlorophenyl)-1,2,4-thiadiazole and 98 mg of 2-butyne-1-ol were dissolved, to the resulting solution was added 56 mg of sodium hydride (60% oily) with ice-cooling, and the mixture was stirred for 30 minutes, and further stirred at room temperature for 1 hour. Then, the reaction mixture was poured into an aqueous saturated sodium chloride solution, and the mixture was extracted with t-butyl methyl ether. The residue obtained by concentration of the organic layer was subjected to silica gel column chromatography to obtain 290 mg of 5-(3-chlorophenyl)-3-(2-butynyloxy)-1,2,4-thiadiazole (the compound (9) of the present invention).

$^1$H-NMR: 7.94 (s, 1H), 7.78 (d, 1H), 7.48 (d, 1H), 7.42 (t, 1H), 5.05 (q, 2H), 1.88 (t, 3H)

PREPARATION EXAMPLE 7

In 2.5 ml of N,N-dimethylformamide, 350 mg of 3-methylsulfonyl-5-(3-chlorophenyl)-1,2,4-thiadiazole and 117 mg of 2-pentyne-1-ol were dissolved, to the resulting solution was added 56 mg of sodium hydride (60% oily) with ice-cooling, and the mixture was stirred for 30 minutes, and further stirred at room temperature for 1 hour. Then, the reaction mixture was poured into an aqueous saturated sodium chloride solution, and the mixture was extracted with t-butyl methyl ether. The residue obtained by concentration of the organic layer was subjected to silica gel column chromatography to obtain 290 mg of 5-(3-chlorophenyl)-3-(2-pentynyloxy)-1,2,4-thiadiazole (the compound (78) of the present invention).

$^1$H-NMR: 7.94 (s, 1H), 7.78 (d, 1H), 7.48 (d, 1H), 7.42 (t, 1H), 5.05 (q, 2H), 1.88 (t, 3H)

PREPARATION EXAMPLE 8

In 3 ml of N,N-dimethylformamide, 400 mg of a mixture of 3-methylsulfonyl-5-(2-chlorophenyl)-1,2,4-thiadiazole and 3-methylsulfinyl-5-(2-chlorophenyl)-1,2,4-thiadiazole and 114 mg of 2-butyne-1-ol were dissolved, to the resulting solution was added 65 mg of sodium hydride (60% oily) with ice-cooling, and the mixture was stirred for 1 hour, and further stirred at room temperature for 1 hour. Then, the reaction mixture was poured into an aqueous saturated sodium chloride solution, and the mixture was extracted with t-butyl methyl ether. The residue obtained by concentration of the organic layer was subjected to silica gel column chromatography to obtain 210 mg of 5-(2-chlorophenyl)-3-(2-butynyloxy)-1,2,4-thiadiazole (the compound (8) of the present invention).

$^1$H-NMR: 8.51 (d, 1H), 7.53 (d, 1H), 7.46 (m, 2H), 5.06 (q, 2H), 1.88 (t, 3H)

PREPARATION EXAMPLE 9

In 3 ml of N,N-dimethylformamide, 400 mg of a mixture of 3-methylsulfonyl-5-(2-chlorophenyl)-1,2,4-thiadiazole and 3-methylsulfinyl-5-(2-chlorophenyl)-1,2,4-thiadiazole, and 136 mg of 2-pentyne-1-ol were dissolved, to the resulting solution was added 65 mg of sodium hydride (60% oily) with ice-cooling, and the mixture was stirred for 1 hour, and further stirred at room temperature for 1 hour. Then, the reaction mixture was added to an aqueous saturated sodium chloride solution, and the mixture was extracted with t-butyl methyl ether. The residue obtained by concentration of the organic layer was subjected to silica gel column chromatography to obtain 220 mg of 5-(2-chlorophenyl)-3-(2-pentynyloxy)-1,2,4-thiadiazole (the compound (77) of the present invention).

$^1$H-NMR: 8.52 (d, 1H), 7.53 (d, 1H), 7.45 (m, 2H), 5.08 (q, 2H), 2.25 (m, 2H), 1.15 (t, 3H)

Then, a process for preparing an intermediate compound of the compound of the present invention will be described as Reference Preparation Example.

REFERENCE PREPARATION EXAMPLE 1

In 30 ml of chloroform, 455 mg of 3-methylthio-5-phenyl-1,2,4-thiadiazole was dissolved, to the resulting solution was added 377 mg of 3-chloroperoxybenzoic acid (65%<), and the mixture was stirred for 7 hours with ice-cooling. Then, the reaction mixture was added to an aqueous sodium bicarbonate solution, and the layers were separated. The organic layer was dried over anhydrous sodium sulfate, and concentrated to obtain 520 mg of a mixture of 3-methylsulfinyl-5-phenyl-1,2,4-thiadiazole and 3-methylsulfonyl-5-phenyl-1,2,4-thiadiazole. This product was used in the next step without further purification.

$^1$H-NMR: 3.13 (sulfinylmethyl s, 3H), 3.44 (sulfonylmethyl s, 3H), 7.55 (m, 3H), 8.00 (m, 2H)

Sulfonyl form:sulfinyl form=1:4

REFERENCE PREPARATION EXAMPLE 2

In 10 ml of chloroform, 330 mg of 3-methylthio-5-(2-fluorophenyl)-1,2,4-thiadiazole was dissolved, to the resulting solution was added 722 mg of 3-chloroperoxybenzoic acid (65%<) with ice-cooling, and the mixture was allowed to stand at room temperature for 18 hours. Then, the reaction mixture was poured into an aqueous sodium bicarbonate solution, and the layers were separated. The organic layer was dried over anhydrous sodium sulfate, and concentrated to obtain 295 mg of a mixture of 3-methylsulfinyl-5-(2-fluorophenyl)-1,2,4-thiadiazole and 3-methylsulfonyl-5-(2-fluorophenyl)-1,2,4-thiadiazole. This product was used in the next step without further purification.

$^1$H-NMR: 3.13 (sulfinylmethyl s, 3H), 3.45 (sulfonylmethyl s, 3H), 7.29-7.41 (m, 2H), 7.59-7.65 (m, 1H), 8.41-8.46 (m, 1H) sulfonyl form:sulfinyl form=4:1

REFERENCE PREPARATION EXAMPLE 3

In 8 ml of chloroform, 360 mg of 3-methylthio-5-(3-fluorophenyl)-1,2,4-thiadiazole was dissolved, to the resulting solution was added 982 mg of 3-chloroperoxybenzoic acid (65%<) with ice-cooling, and the mixture was stirred at room temperature for 7 hours. The reaction mixture was poured into an aqueous sodium sulfite solution, and the layers were separated. The organic layer was washed with an aqueous sodium bicarbonate solution, dried over anhydrous sodium sulfate, and concentrated to obtain 520 mg of 3-methylsulfonyl-5-(3-fluorophenyl)-1,2,4-thiadiazole.

$^1$H-NMR: 3.45 (s, 3H), 7.27-7.47 (m, 1H), 7.49-7.58 (m, 1H), 7.73-7.81 (m, 1H)

REFERENCE PREPARATION EXAMPLE 4

To 30 ml of toluene were added 500 mg of 5-chloro-3-methylthio-1,2,4-thiadiazole, 794 mg of trimethylphenyltin and 346 mg of tetrakistriphenylphosphine palladium, and the mixture was heated under reflux for 8 hours in a nitrogen atmosphere. Then, the reaction mixture was cooled to room temperature, and a 20% aqueous potassium fluoride solution was added to the reaction mixture, followed by stirring. This mixture was filtered through Celite, and the filtrate was concentrated. The resulting residue was subjected to silica gel column chromatography to obtain 455 mg of 3-methylthio-5-phenyl-1,2,4-thiadiazole.

mp: 57.1° C.

REFERENCE PREPARATION EXAMPLE 5

To 4 ml of 1,2-dimethoxyethane were added 300 mg of 5-chloro-3-methylthio-1,2,4-thiadiazole, 427 mg of 2,3-difluorophenylboronic acid, 104 mg of tetrakistriphenylphosphine palladium and 4 ml of a 2 M aqueous sodium carbonate solution, and the mixture was stirred at 60° C. for 9 hours in a nitrogen atmosphere. Then, the reaction mixture was poured into an aqueous saturated sodium chloride solution, and the mixture was extracted with t-butyl methyl ether. The residue obtained by concentration of the organic layer was subjected to silica gel column chromatography to obtain 170 mg of 3-methylthio-5-(2,3-difluorophenyl)-1,2,4-tihadiazole.

$^1$H-NMR: 2.73 (s, 3H), 7.26-7.38 (m, 2H), 8.05-8.11 (m, 1H)

REFERENCE PREPARATION EXAMPLE 6

To 4 ml of 1,2-dimethoxyethane were added 284 mg of 5-chloro-3-methylthio-1,2,4-thiadiazole, 262 mg of 2-fluorophenylboronic acid, 98 mg of tetrakistriphenylphosphine palladium and 4 ml of a 2 M aqueous sodium carbonate solution, and the mixture was stirred at 80° C. for 12 hours in a nitrogen atmosphere. Then, the reaction mixture was poured into an aqueous saturated sodium chloride solution, and the mixture was extracted with t-butyl methyl ether. The residue obtained by concentration of the organic layer was subjected to silica gel column chromatography to obtain 330 mg of 3-methylthio-5-(2-fluorophenyl)-1,2,4-thiadiazole.

$^1$H-NMR: 2.74 (s, 3H), 7.21-7.34 (m, 2H), 7.49-7.56 (m, 1H), 8.30-8.36 (m, 1H)

REFERENCE PREPARATION EXAMPLE 7

To 5 ml of 1,2-dimethoxyethane were added 400 mg of 5-chloro-3-methylthio-1,2,4-thiadiazole, 335 mg of 3-fluorophenylboronic acid, 139 mg of tetrakistriphenylphosphine palladium and 4 ml of a 2 M aqueous sodium carbonate solution, and the mixture was heated under reflux for 2 hours in a nitrogen atmosphere. Then, the reaction mixture was poured into water, and the mixture was extracted with t-butyl methyl ether. The residue obtained by concentration of the organic layer was subjected to silica gel column chromatography to obtain 360 mg of 3-methyothio-5-(3-fluorophenyl)-1,2,4-thiadiazole.

REFERENCE PREPARATION EXAMPLE 8

To 25 ml of 1,2-dimethoxyethane were added 2.0 g of 5-chloro-3-methylthio-1,2,4-thiadiazole, 2.25 g of 3-chlorophenylboronic acid, 694 mg of tetrakistriphenylphosphine palladium and about 25 ml of a 2 M aqueous sodium carbonate solution, and the mixture was heated under reflux for 3 hours in a nitrogen atmosphere. Then, the reaction mixture was poured into water, and the mixture was extracted with t-butyl methyl ether. The organic layer was dried with anhydrous sodium sulfate, and the residue obtained by concentration was subjected to silica gel column chromatography to obtain 1.48 g of 3-methylthio-5-(2-chlorophenyl)-1,2,4-thiadiazole.

$^1$H-NMR: 7.95 (s, 1H), 7.78 (d, 1H), 7.49 (d, 1H), 7.42 (t, 1H), 2.73 (s, 3H)

REFERENCE PREPARATION EXAMPLE 9

In 12 ml of chloroform, 1.5 g of 3-methylthio-5-(3-chlorophenyl)-1,2,4-thiadiazole was dissolved, to the resulting solution was slowly added 5.85 g of 3-chloroperoxybenzoic acid (65%<) with ice-cooling, and the mixture was stirred for 30 minutes with ice-cooling, and at room temperature for 2 hours. The reaction mixture was poured into an aqueous sodium sulfite solution, and the layers were separated. The organic layer was washed with an aqueous sodium bicarbonate solution, dried over anhydrous sodium sulfate, and concentrated to obtain 1.44 g of 3-methylsulfonyl-5-(3-chlorophenyl)-1,2,4-thiadiazole.

$^1$H-NMR: 8.04 (s, 1H), 7.88 (d, 1H), 7.59 (d, 1H), 7.7.49 (t, 1H), 3.32 (s, 3H)

REFERENCE PREPARATION EXAMPLE 10

To 25 ml of 1,2-dimethoxyethane were added about 2.0 g of 5-chloro-3-methylthio-1,2,4-thiadiazole, 2.25 g of 2-chlorophenylboronic acid, 694 mg of tetrakistriphenylphosphine palladium and 25 ml of a 2 M aqueous sodium carbonate solution, and the mixture was heated under reflux for 3 hours in a nitrogen atmosphere. Then, the reaction mixture was poured into water, and the mixture was extracted with t-butyl methyl ether. The organic layer was dried over anhydrous sodium sulfate, and the residue obtained by concentration was subjected to silica gel column chromatography to obtain 1.67 g of 3-methylthio-5-(3-chlorophenyl)-1,2,4-thiadiazole.

REFERENCE PREPARATION EXAMPLE 11

In 30 ml of chloroform, 1.5 g of 3-methylthio-5-(2-chlorophenyl)-1,2,4-thiadiazole was dissolved, to the resulting solution was slowly added 3.05 g of 3-chloroperoxybenzoic acid (70%<) with ice-cooling, and the mixture was stirred for 30 minutes with ice-cooling, and at room temperature for 2 hours. The reaction mixture was poured into an aqueous sodium sulfite solution, and the layers were separated. The organic layer was washed with an aqueous sodium bicarbonate solution, dried over anhydrous sodium sulfate, and concentrated to obtain 1.61 g of a mixture of 3-methylsulfonyl-5-(2-chlorophenyl)-1,2,4-thiadiazole and 3-methylsulfinyl-5-(2-chlorophenyl)-1,2,4-thiadiazole.

$^1$H-NMR: 8.64-8.58 (m), 7.60-7.48 (m), 3.45 (s), 3.13 (s)

sulfonyl form:sulfinyl form=about 2.7:1

Then, Formulation Examples will be shown. Hereinafter, parts represent parts by weight and the compound of the present invention is expressed by compound No. shown in Table 1.

FORMULATION EXAMPLE 1

Emulsion

In 37.5 parts of xylene and 37.5 parts of dimethylformamide, 9 parts of each of the compounds (1) to (140) of the present invention is dissolved, 10 parts of polyoxyethylenestyryl phenyl ether and 6 parts of calcium dodecylbenzenesulfonate are added thereto, and the mixture is thoroughly stirred and mixed to obtain an emulsion.

FORMULATION EXAMPLE 2

Wettable Powder

To a mixture of 4 parts of sodium lauryl sulfate, 2 parts of calcium lignin sulfonate, 20 parts of a synthetic hydrated silicon oxide fine powder and 65 parts of diatomaceous earth, 9 parts of each of the compounds (1) to (140) of the present invention is added, and the mixture is thoroughly stirred and mixed to obtain a wettable powder.

FORMULATION EXAMPLE 3

Granule

A mixture of 3 parts of each of the compounds (1) to (140) of the present invention, 5 parts of a synthetic hydrated silicon oxide fine powder, 5 parts of sodium dodecylbenzenesulfonate, 30 parts of bentonite and 57 parts of clay is thoroughly stirred and mixed, and an appropriate amount of water is added to the mixture. The mixture is further stirred, subjected to granulation with a granulator, and air-dried to obtain a granule.

FORMULATION EXAMPLE 4

Powder

A mixture of 4.5 parts of each of the compounds (1) to (140) of the present invention, 1 part of a synthetic hydrated silicon oxide fine powder, 1 part of Dolires B (Sankyo Co., Ltd.) as a coagulating agent, and 7 parts of clay is thoroughly mixed with a mortar, and then stirred and mixed with a juice mixer. To the resulting mixture is added 86.5 parts of cut clay, and the mixture is thoroughly stirred and mixed to obtain a powder.

FORMULATION EXAMPLE 5

A mixture of 10 parts of each of the compounds (1) to (140), 35 parts of white carbon containing 50 parts of polyoxyethylene alkyl ether sulfate ammonium salt, and 55 parts of water is finely ground by a wet grinding method to obtain a preparation.

Then, Test Examples demonstrate that the compound of the present invention is effective as an active ingredient of a harmful arthropod controlling composition.

TEST EXAMPLE 1

A preparation prepared from each of the compounds (1), (2), (5), (6) and (16) of the present invention according to Formulation Example 5 was diluted with water so that the concentration of the compound of the present invention became 500 ppm to obtain a test scattering solution.

On the other hand, soil was filled in a polyethylene cups, cucumber was planted in each cup, and grown until its first foliage leaves developed. About 20 cotton aphids (*Aphis gossypii*) were made parasitic on the cucumber. After one day, the aforementioned test scattering solution was scattered on the cucumber at a ratio of 20 ml/cup. Six days after scattering, the number of cotton aphids was examined, and a controlling value was calculated by the following equation.

Controlling value (%)={1−($Cb$×$Tai$)/($Cai$×$Tb$)}×100 wherein Cb represents the number of insects of an untreated group before treatment, Cai represents the number of insects of an untreated group at the time of observation, Tb represents the number of insects of a treated group before treatment, and Tai represents the number of insects of a treated group at the time of observation, respectively.

As a result, all of the compounds (1), (2), (5), (6) and (16) of the present invention showed a controlling value of 90% or more, respectively.

TEST EXAMPLE 2

A preparation prepared from each of the compound (1) of the present invention and a comparative compound (A) according to Formulation Example 5 was diluted with water so that the concentration of the compound of the present invention became 500 ppm to obtain a test scattering solution.

On the other hand, soil was filled into polyethylene cups, cucumber was planted in each cup, and grown until its first foliage leaves developed. The aforementioned test scattering solution was scattered on the cucumber at a ratio of 20 ml/cup, and the scattered solution on the surface of the leaf was dried. The first foliage leaf was cut off, placed on a filter (diameter 70 mm) impregnated with water in a polyethylene cup (diameter 110 mm), 30 larvae of western flower thrips (*Frankliniella occidentalis*) were released thereon, and the polyethylene cup was closed with a lid. After seven days, a damage degree of the cucumber leaf by western flower thrips (*Frankliniella occidentalis*) was examined.

As a result, a damage area rate by western flower thrips (*Frankliniella occidentalis*) in the leaf treated with the compound (1) of the present invention was within 5%. A damage area rate in the leaf treated with the comparative compound (A) was 20% or more.

TEST EXAMPLE 3

A preparation prepared from each of the compounds (1), (2), (5), (6), (8), (9), (16), (77) and (78) of the present invention and the comparative compound (A) according to Formulation Example 5 was diluted with water so that the concentration of the compound of the present invention became 500 ppm to obtain a test scattering solution.

On the other hand, soil was filled in polyethylene cups, cabbage was planted in each cup, and grown until its first foliage leaves developed, and leaves other than a first foliage leaves were removed. About 200 imagoes of silverleaf whitefly (*Bemisia* argentifolii) were released on this cabbage for about 24 hours, and had them lay eggs on the cabbage first foliage leaf.

The thus obtained cabbage on which about 80 to 100 eggs of silverleaf whitefly (*Bemisia argentifolii*) were laid was allowed to stand in a greenhouse for 8 days, and the aforementioned test scattering solution was scattered at a ratio of 20 ml/cup. Seven days after scattering, the number of alive insects was examined, and an insecticidal rate was calculated. As a result, the compounds (1), (2), (5), (6), (8), (9), (16), (77) and (78) of the present invention showed an insecticidal rate of 90% or more. The comparative compound (A) showed an insecticidal rate of 30% or less.

The comparative compound (A) used in Test Example 2 and Test Example 3 is a compound represented by the following formula described in DE3030661 (compound 9 in the table on page 47).

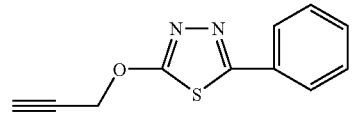

INDUSTRIAL APPLICABILITY

By using the compound of the present invention, harmful arthropods can be controlled.

The invention claimed is:

1. A 1,2,4-thiadiazole compound represented by the formula (1):

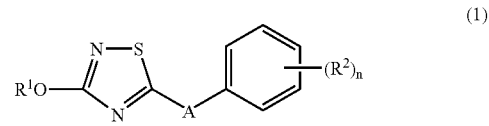

wherein $R^1$ represents a C3-C7 alkynyl group optionally substituted with one or more halogen atom(s), $R^2$ represents a halogen atom, a C1-C4 alkyl group, a C1-C4 haloalkyl group, a C1-C4 alkoxy group, a C1-C4 haloalkoxy group, a C1-C4 alkylthio group, a cyano group or a nitro group, n represents an integer of 0 to 5, provided that, when n represents an integer of 2 or more, respective $R^2$s may be the same or different, A represents an oxygen atom, a sulfur atom, a single bond, a $CR^3R^4$ group or a $NR^5$ group, $R^3$ and $R^4$ represent each independently a hydrogen atom or a C1-C4 alkyl group, and $R^5$ represents a hydrogen atom, a C1-C7 alkyl group, a haloalkyl group, a C2-C4(alkoxyalkyl) group, a C2-C4(haloalkoxyalkyl) group, a C3-C6 alkenyl group, a C3-C6 haloalkenyl group, a C3-C7 alkynyl group, a C3-C7 haloalkynyl group or a cyanomethyl group.

2. The 1,2,4-thiadiazole compound according to claim 1, wherein A in the formula (1) is a single bond.

3. The 1,2,4-thiadiazole compound according to claim 1, wherein $R^1$ in the formula (1) is a 2-propynyl group, a 2-butynyl group or 2-pentynyl group.

4. The 1,2,4-thiadiazole compound according to claim 1, wherein $R^1$ in the formula (1) is a 2-butynyl group or a 2-pentynyl group.

5. A composition for controlling a harmful arthropod which comprises an effective amount of the 1,2,4-thiadiazole compound according to claim 1.

6. A method for controlling a harmful arthropod which comprises applying, to harmful arthropods or a place where harmful arthropods inhabit, a 1,2,4-thiadiazole compound represented by the formula (1):

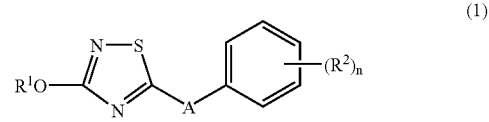

wherein $R^1$ represents a C3-C7 alkynyl group optionally substituted with one or more halogen atom(s), R represents a halogen atom, a C1-C4 alkyl group, a C1-C4 haloalkyl group, a C1-C4 alkoxy group, a C1-C4 haloalkoxy group, a C1-C4 alkylthio group, a cyano group or a nitro group, n represents an integer of 0 to 5, provided that, when n represents an integer of 2 or more, respective $R^2$s may be the same or different, A represents an oxygen atom, a sulfur atom, a single bond, a $CR^3R^4$ group or a $NR^5$ group, $R^3$ and $R^4$ represent each independently a hydrogen atom or C1-C4 alkyl group, and $R^5$ represents a hydrogen atom, a C1-C7 alkyl group, a haloalkyl group, a C2-C4(alkoxyalkyl) group, a C2-C4(haloalkoxyalkyl) group, a C3-C6 alkenyl group, a C3-C6 haloalkenyl group, a C3-C7 alkynyl group, a C3-C7 haloalkynyl group or a cyanomethyl group.

7. The controlling method according to claim 6, wherein the harmful arthropod is a Hemiptera insect pest, a Lepidoptera insect pest, a Coleoptera insect pest or a Thysanoptera insect pest.

8. The controlling method according to claim 6, wherein the harmful arthropod is a Hemiptera insect pest or a Thysanoptera insect pest.

9. The 1,2,4-thiadiazole compound according to claim 2, wherein $R^1$ in the formula (1) is a 2-propynyl group, a 2-butynyl group or 2-pentynyl group.

10. The 1,2,4-thiadiazole compound according to claim 2, wherein $R^1$ in the formula (1) is a 2-butynyl group or a 2-pentynyl group.

* * * * *